United States Patent
Nepras et al.

(10) Patent No.: US 8,692,005 B2
(45) Date of Patent: Apr. 8, 2014

(54) CATALYST FOR ESTERAMINE PRODUCTION

(75) Inventors: Marshall J. Nepras, Burlington, WI (US); Franz J. Luxem, Palatine, IL (US); Leonard F. Zaporowski, Chicago, IL (US); David Eisenberg, Northbrook, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/586,023

(22) Filed: Aug. 15, 2012

(65) Prior Publication Data

US 2012/0309993 A1  Dec. 6, 2012

Related U.S. Application Data

(63) Continuation of application No. PCT/US2011/024907, filed on Feb. 15, 2011.

(60) Provisional application No. 61/304,713, filed on Feb. 15, 2010.

(51) Int. Cl.
    *C07C 227/00* (2006.01)
(52) U.S. Cl.
    USPC ............ 554/114; 564/174; 564/169; 564/103
(58) Field of Classification Search
    None
    See application file for complete search history.

(56) References Cited

U.S. PATENT DOCUMENTS

| 2,989,499 | A | | 6/1961 | Linville et al. |
| 3,320,292 | A | * | 5/1967 | Cahn et al. ............... 554/92 |
| 4,690,783 | A | | 9/1987 | Johnson, Jr. |
| 5,637,743 | A | | 6/1997 | Contet et al. |
| 5,908,946 | A | | 6/1999 | Stern et al. |
| 6,458,173 | B1 | | 10/2002 | Lin |
| 2002/0002298 | A1 | * | 1/2002 | Bigorra Llosas et al. ..... 554/114 |
| 2002/0025915 | A1 | | 2/2002 | Franklin et al. |
| 2006/0167144 | A1 | | 7/2006 | Borade et al. |
| 2009/0169677 | A1 | | 7/2009 | Wittorff et al. |
| 2010/0016163 | A1 | | 1/2010 | Keiper et al. |

FOREIGN PATENT DOCUMENTS

JP  05-148198  *  6/1993  ............ C07C 219/06

OTHER PUBLICATIONS

JP 05-148198, Lion, Corp., Production of nitrogen-containing fatty acid ester and production of ester group-containing quarternary ammonium salt, 1993, English Translation, 9 pages.*
International Search Report and Written Opinion in PCT/US2011/024907, mailed Apr. 11, 2011.
International Preliminary Report on Patentability in PCT/US2011/024907, mailed Aug. 30, 2012.

* cited by examiner

*Primary Examiner* — Yate K Cutliff
(74) *Attorney, Agent, or Firm* — McAndrews, Held & Malloy, Ltd.

(57) ABSTRACT

Provided are methods for decreasing the reaction time between an alkanolamine such as triethanolamine and a fatty acid alkyl ester such as, a triglyceride, a vegetable oil, a methyl ester, an ethyl ester, etc., a fatty acid, or a mixture thereof. The methods utilize a divalent zinc catalyst to facilitate and accelerate an esterification or transesterification reaction between the alkanolamine and the fatty acid, or fatty acid alkyl ester.

17 Claims, No Drawings

CATALYST FOR ESTERAMINE PRODUCTION

BACKGROUND OF THE INVENTION

This application is a continuation of International application Serial No. PCT/US2011/024907 (International Publication No. WO/2011/100746), having an international filing date of Feb. 15, 2011. This PCT application claims priority to and claims benefit from U.S. provisional patent application Ser. No. 61/304,713, filed on Feb. 15, 2010. The entire specifications of the PCT and provisional applications referred to above are hereby incorporated by reference.

The presently described technology relates generally to a method for producing esteramines through transesterification or esterification processing between alkanolamines and alkyl esters or fatty acids. More specifically, the present technology provides methods for decreasing the reaction time and/or lowering the reaction temperature needed to react alkanolamines and fatty acid alkyl esters, fatty acids, or mixtures thereof through utilization of zinc catalysts.

Esterification reactions of alkanolamines with carboxylic acids or fatty acids have traditionally been catalyzed with an acid catalyst, such as, for example, phosphorous acid, sulfuric acid, or the starting carboxylic acid itself. Such acid catalysts have several drawbacks, including a very slow reaction time.

Sodium or potassium alkoxides (e.g., methoxides), in general, are also used with alkyl esters for transesterification reaction processing. Such processes are seriously inhibited, however, by moisture and/or acidic impurities. These types of alkoxides also produce resultant transesterified products that, in many instances, exhibit the viscosity of a gel, due to side reactions. Potassium hydroxide is often used to catalyze the reaction between triglycerides and triethanolamine. However, the reaction is still very slow and is believed by those skilled in the art to be due, in part, to the potassium hydroxide immediately reacting with acidic impurities during reaction processing to generate water and other potassium salts, which may, or may not, be of any use as catalysts.

Titanium catalysts, sold commercially under the brand name TYZOR® have also been used to catalyze the reaction of triethanolamine and fatty acid. Such titanium catalysts, however, also have several drawbacks. In particular, titanium catalysts tend to form titanium precipitates in solution. Residual titanium catalysts can also interfere with product stability and result in a poorly colored product that may require further bleaching. In addition, when titanium catalysts are used with triethanolamine and fatty acid, the resulting ratios of monester, diester and triester esteramines are not in line with established product specifications. Further, it is known that the activity of titanium catalysts are negatively impacted by amines in the absence of carboxylic acids. This affect, is a hindrance when a carboxylic acid feed is replaced by an alkyl ester feed such as methylester, in conducting the reaction to produce the esteramine.

In view of the above drawbacks, there is a need for an improved catalyst that can decrease the esterification or transesterification reaction time for the reaction between alkanolamines and carboxylic acids or fatty acids, or alkyl esters. There is also a need for a catalyst that can produce an esteramine product that is storage stable, has a good color, and has ratios of monoester, diester and triester esteramines that meet existing product specifications for esteramines.

BRIEF SUMMARY OF THE INVENTION

In one aspect, the presently described technology provides a method for decreasing the reaction time between an alkanolamine and a fatty acid alkyl ester, a fatty acid, or a mixture thereof by utilizing a divalent zinc catalyst. In accordance with at least one embodiment of the present technology, the transesterification or esterification reaction can proceed to completion substantively faster than, and in some cases twice as fast as when conventional catalysts are used.

Suitable alkanolamines include, for example, ethanolamine, diethanolamine, triethanolamine, isopropanolamine, diisopropanolamine, triisopropanolamine, alkyldiethanolamines, alkyldiisopropanolamines, dialkylmonoethanolamines, dialkylmonoisopropanolamines, and combinations thereof. Preferred alkanolamines for the presently described technology are dimethylethanolamine (DMEA) methydiethanolamine (MDEA) and triethanolamine (TEA). Examples of suitable fatty acid alkyl esters and fatty acids include triglycerides, vegetable oils, fatty acid methylesters, fatty acid ethylesters, stearic acid, tallow fatty acid, derivatives thereof, and combinations thereof.

The divalent zinc catalyst is added in a usable form to the reaction mixture so that the zinc can be soluble in order for homogeneous catalysis to occur. In some embodiments, the divalent zinc catalyst is in the form of zinc oxide, zinc carbonate, or zinc diphosphinate. In other embodiments, the divalent zinc is in the form of a zinc salt.

The resulting esteramines of the present technology can be derivitized with a quaternizing agent, such as, for example, methyl chloride or dimethyl sulfate in order to produce a fabric softener or anti-static agent. Other quaternizing agents can also be used, such as epichlorohydrin, or derivatives thereof, such as 3-chloro-2-hydroxypropanesulfonate, sodium salt.

DETAILED DESCRIPTION OF THE INVENTION

The presently described technology relates generally to a method for producing esteramines through the transesterification or esterification reaction of alkanolamines and alkyl esters, fatty acids, or mixtures thereof. More specifically, the present technology provides a method for decreasing the reaction time between alkanolamines (e.g., triethanolamine) and fatty acid alkyl esters (e.g., triglycerides, vegetable oils, fatty acid methylesters, fatty acid ethylesters, etc.), fatty acids, or mixtures thereof.

In one aspect, the presently described technology utilizes a divalent zinc catalyst in at least one esterification or transesterification reaction to produce an esteramine. By divalent zinc is meant zinc in its $^{+2}$ oxidation state. The divalent zinc should be added in a usable form to the reaction mixture so that the zinc can become soluble in order for homogeneous catalysis to occur. For starting reaction mixtures of fatty acid or carboxylic acid and alkanolamine, the zinc catalyst can be added in the form of zinc oxide or any other zinc compound which can supply a soluble form of divalent zinc to the reaction mixture, these include but are not limited to zinc salts such as zinc carbonate or zinc triflate. The zinc oxide is then rapidly converted by the molten carboxylic acid to zinc dicarboxylate, or if stearic acid is used as the fatty acid, the zinc oxide is converted to zinc distearate. Zinc salts of phosphinic acid, such as zinc diphosphinate can also be used as the catalyst. Zinc diphosphinate can be made in situ or, alternatively from a separate reaction of zinc oxide and phosphinic acid. Other zinc catalysts, such as zinc carbonate and zinc triflate, can also be used. For starting reaction mixtures of fatty alkyl ester and an alkanolamine, the divalent zinc should be added in the form of a soluble salt, since zinc oxide or zinc carbonate are not sufficiently soluble in this starting mixture to generate a workable divalent homogeneous zinc catalyst.

Suitable zinc salts for use as the catalyst for the alkyl ester transesterification reaction of fatty alkyl ester and alkanolamine include zinc acetate or zinc diphosphinate.

It has been surprisingly found that the divalent zinc catalyst of the present technology can unexpectedly improve esterification or transesterification speed/reaction time. For example, when divalent zinc is used as the catalyst in accordance with at least one embodiment of the present technology, the esterification or transesterification reaction can proceed to completion, on average, twice as fast as when other catalysts are used in place of divalent zinc when compared on a molar basis.

In accordance with one or more embodiments, the divalent zinc catalysts of the present technology can also visually improve the color of the resultant esteramine materials such that a subsequently quaternized material can be of improved color also. This can, for example, make an additional bleaching step unnecessary when producing products according to the present technology.

In accordance with some embodiments of the present technology, the divalent zinc catalysts can produce esteramine products that are free of precipitates and that also have superior storage stability compared to esteramine products prepared by using other catalysts.

A further advantage of the divalent zinc catalysts of the present technology is that, with respect to the reaction of triethanolamine and fatty acid, the resulting mole ratios of monoester, diester and triester esteramines in the final product mixture are consistent with the established product specifications for esteramines that were obtained from the well established Brønsted acid catalysis.

As is well known, when triethanolamine is the starting amine and is made to react with carboxylic acids or alkylesters, the resulting esteramines are composed of a mixture of monoesterified, diesterified, and triesterified esteramines. This mixture is made possible due to the fact that triethanolamine contains three identical alcohols, each of which can react with a fatty acid or fatty alkyl ester to generate the ester bonds. When the divalent zinc catalyst of the present technology is employed instead of a traditional acid or base catalyst, the final product mixtures have an identical mixture composition of monoester, diester and triester esteramines, as compared to mixtures obtained from traditional Brønsted catalysts, yet the overall esterification reaction proceeds at a much faster rate.

Similarly, when methyldiethanolamine is the starting amine and made to react with a carboxylic acid or alkylesters, the resulting esteramines are composed of a mixture of monoesterified and diesterified esteramines. This mixture is made possible due to the fact that methyl diethanolamine contains two identical alcohols, each of which can react with a fatty acid, or fatty alkyl ester, to generate the ester bonds. When divalent zinc is employed as the catalyst instead of a traditional Brønsted acid catalyst, the final product mixtures have an identical composition mixture of monoester and diester esteramines compared to mixtures obtained from traditional Brønsted catalysts, but the overall esterification reaction proceeds at a much faster rate.

When dimethylmonoethanolamine is the starting amine, the resulting esteramine is the monoesterified esteramine because the lone alcohol can react with a fatty acid or fatty alkyl ester to generate the ester bond. When divalent zinc is used as the catalyst instead of a traditional Brønsted acid catalyst, the esterification reaction proceeds at a much faster rate.

In accordance with some embodiments, the divalent zinc catalysts of the present technology are also surprisingly active in the presence of moisture and/or acidic materials, which may be present in feedstocks utilized for reaction processing. This acidic material may be, for example, residual fatty acid. In accordance with one or more embodiments, the divalent zinc catalysts of the present technology can also prevent gelling of the resultant esteramines by minimizing side reactions, which often occur when stronger bases are used to catalyze transesterification reactions.

Another advantage of the divalent zinc catalyst of the present technology is that it does not become deactivated by amines. The problem with Brønsted acid catalysis in the presence of amines is that the acids quickly become deactivated due to proton transfer from the acid to the nitrogen on the amine. The strong nature of the acid catalysts, as compared to the weaker carboxylic acids, causes them to lose their proton preferentially to the amine, thus preventing strong acid proton availability for catalysis. This transfer makes the proton largely unavailable to perform any catalysis on the moieties which are crucial to the esterification reaction. On the other hand, catalysis by metals is possible and the metals are known to be coordinated Lewis acids. Surprisingly, divalent zinc is an effective catalyst and does not become deactivated by amines. This development is a surprise, since amines are known to coordinate to divalent zinc, or metal ions in general, but this apparently does not significantly hinder the catalysis of the esterification reaction for zinc. Without being bound by theory, it is believed that divalent zinc can act as a Lewis acid without changing the pH of the reaction media. Divalent zinc catalysts are therefore superior to protic acids, because: 1) divalent zinc may induce multiple positive charges into reactants, while a proton can induce only a single positive charge, 2) divalent zinc can exist in neutral media not just acidic solutions, which can minimize unwanted side reactions, and 3) divalent zinc can coordinate to several electron donor atoms simultaneously, whereas a proton usually coordinates to only one donor atom.

Suitable starting fatty acid esters for the present technology include, for example, fatty acid alkyl esters, and may contain any combination of fatty acid alkyl groups having from about 2 to about 30, alternatively from about 5 to about 25 carbon atoms. The fatty acid alkyl groups can be either saturated or unsaturated or partially hydrogenated. The ester alkyl groups (i.e., the alkyl groups utilized to form esters with the fatty acid) may be complex or simple, and can also contain alkyl groups, with or without branching, having from about 1 to about 30, alternatively from about 1 to about 25, alternatively from about 1 to about 4 carbon atoms. The ester alkyl groups may contain multiple hydroxides, free or functionalized. Examples of suitable starting fatty acid esters include, but are not limited to, triglycerides, vegetable oils, fatty acid methylesters, fatty acid ethylesters, derivatives thereof, and combinations thereof.

Suitable starting fatty acids for the present technology can be, for example, any alkyl acid having from about 2 to about 30, alternatively from about 5 to about 25 carbon atoms, and can be saturated or unsaturated or partially hydrogenated.

Suitable alkanolamines for the present technology include, for example, ethanolamine, diethanolamine, triethanolamine, isopropanolamine, diisopropanolamine, triisopropanolamine, alkyldiethanolamines, alkyldiisopropanolamines, dialkyl monoethanolamines, dialkylmonoisopropanolamines, and combinations thereof. The alkyl groups in the alkanolamines may contain from about 1 to about 30 carbon atoms, and can be saturated or unsaturated, linear, cyclic, or aromatic. Preferred alkanolamines for the present technology include methyldiethanolamine and triethanolamine.

Preferably, the combined catalyst and starting materials including the alkanolamines and fatty alkyl esters can be heated to a temperature of from about 60° C. to about 300° C., alternatively from about 130° C. to about 190° C., alternatively from about 150° C. to about 200° C. Besides conducting the reaction at a conventional transesterification reaction temperature, it has been surprisingly found that the divalent zinc catalyst of the present technology can unexpectedly lower the required reaction temperature, while still keeping the reaction at a commercially viable or improved speed. Among other benefits, to conduct the transesterification reaction at a lower temperature can not only save energy costs but also reduce side reactions and the amount of undesired side products.

In accordance with some embodiments of present technology, the esterification reaction can be conducted within one preferred temperature range. In accordance with some other embodiments of present technology, the esterification reaction can be conducted within a first preferred temperature range for a period of time, and then within another preferred temperature range for another period of time, and there can be two or more such periods.

Preferably, the molar ratio of alkanolamine and alkyl esters, fatty acids, or mixtures thereof, where the alkanolamine is in the denominator of the ratio, can be from about 0.5/1 to 3/1, alternatively about 1.5/1 to about 2.0/1, alternatively about 1.7/1 to about 2.0/1, alternatively 1.7/1 to 1.75/1, alternatively about 1.88/1 to about 1.92/1.

The divalent zinc catalysts of the present technology can be added either before or after the reaction temperature has been reached. The amount of catalyst contained in the reaction mixture should be an effective amount of divalent zinc metal greater than 1 ppm and calculated from the total weight of reactants, preferably from about 20 ppm to about 5000 ppm by weight, most preferably at about 100 ppm to about 200 ppm. Usually, but not necessarily, the reaction occurs in the presence of an inert atmosphere such as, but not limited to, nitrogen.

In some embodiments of the present technology, when the starting material requires, a vacuum system can be attached to the reaction system in order to remove, for example, volatile alcohols, products, or by-products during the course of the esterification or transesterification reaction.

The divalent zinc catalyst is an improved or superior catalyst for the esterification reaction of alkanolamines with fatty carboxylic acids or carboxylic acids, and the transesterification reaction of alkanolamines with fatty alkyl esters or methyl esters or esters generally. It has also been surprisingly observed that the divalent zinc catalyst is also affected by the structure of the alkanolamines, during the course of the esterification or transesterification reactions, thus, a relative reactivity scale is as follows: polyolalkylamine>>>triolalkylamine>>diolalkylamine>monoalkanolamine. Without being bound by theory it is believed that the divalent zinc is chelated by the alkanolamines, in such a way, as to better facilitate the esterification or transesterification reactions. In addition, it is also believed that the zinc catalyst could be used to catalyze the esterification reaction of (1) fatty or carboxylic acids with alcohols, or (2) fatty alkyl esters or methyl esters with alcohols.

The present technology will be better understood by reference to the following examples. These examples are provided to describe specific embodiments of the invention and to demonstrate specific aspects of the present technology. By providing these specific examples, the inventors do not limit the scope of the invention.

EXAMPLES

Example 1A

Tea/Fatty Acid Based Esteramine Synthesis with Zinc Derived from ZNO

Tallow fatty acid (1740.9 grams, MW=272.0, 6.400 mole) was placed into the large 3-liter resin kettle reactor at 87° C., under a blanket of nitrogen with 2.1709 grams of Anox 20. The zinc oxide (Sunsmart, lot#189, 0.3575 grams) was added to the fatty acid. This amount of ZnO gave a pre-reaction Zinc concentration of 125 ppm. Triethanolamine (TEA), 554.2795 grams (MW=149.19, 3.7149 mole) was added to the flask, and the mole ratio of fatty acid/TEA was calculated to be 1.72/1. The nitrogen was regulated and subsurface sparged at a rate of 175 mL/min. The mixture was stirred. A vacuum was used to remove the excess oxygen, with the application of 80 mmHg vacuum followed by nitrogen release; this cycle was applied twice. The mixture was heated until a temperature of 180° C. was reached. The majority of the water was condensed at atmospheric pressure with the help of an air cooled condenser, before 150° C. was reached. At 150° C., the vacuum was applied at 83 mmHg. Samples of crude esteramine were collected at intervals and titrated for residual fatty acid with a visual phenolphthalein endpoint using 0.1002N KOH/Methanol. The expected free fatty acid range was 0.11-0.08 mEq/g. The reaction reached completion 0.75 hour after the temperature of 180° C. was reached.

Example 1B

Tea/Fatty Acid Based Esteramine Synthesis without Zinc

Tallow fatty acid (1733.7 grams, MW=272.0, 6.374 mole) was placed into the large 3-liter resin kettle reactor at 87° C., under a blanket of nitrogen with 2.1609 grams of Anox 20. Triethanolamine (TEA), 551.9269 grams (MW=149.19, 3.6995 mole) was added to the flask, and the mole ratio of fatty acid/TEA was calculated to be 1.72/1. The nitrogen was regulated and subsurface sparged at a rate of 175 mL/min. The mixture was stirred. A vacuum was used to remove the excess oxygen, with the application of 80 mmHg vacuum followed by nitrogen release; this cycle was applied twice. The mixture was heated until a temperature of 180° C. was reached. The majority of the water was condensed at atmospheric pressure with the help of an air cooled condenser before 150° C. was reached. At 150° C., a vacuum was applied at 83 mmHg. Samples of crude esteramine were collected at intervals and titrated for residual fatty acid with a visual phenolphthalein endpoint using 0.1002N KOH/Methanol. The expected free fatty acid range was 0.11-0.08 mEq/g. The reaction reached completion 1.37 hours after the temperature of 180° C. was reached.

Example 2A

Tea/fatty Acid Based Esteramine Synthesis with Zinc Derived from Zinc Triflate

Tallow fatty acid, 332.3 grams (MW=272.0, 1.222 mole) was placed into a small 4-neck round bottom flask, under a blanket of nitrogen. Triethanolamine (TEA), 95.9 grams (MW=149.19, 0.643 mole) was added to the flask, and the mole ratio of fat/TEA was calculated to be 1.90/1. The mixture was stirred. The temperature of the mixture was increased to 130° C., at which point, zinc triflate 98% (Aldrich, MW=363.51, 0.2501 g, 0.000688 mole) was added and the reactor, which was then sealed under nitrogen. The pre-reaction zinc content was calculated to be 105 ppm. The nitrogen was subsurface sparged at a rate of 200 ml/min. The mixture was heated until a temperature of 170° C. was reached. At 156° C., the rapid evolution of water was observed, and the water was condensed with the help of an air cooled condenser. Samples of crude esteramine were collected at intervals and titrated for residual fatty acid with a visual phenolphthalein endpoint using 0.1000N KOH/Methanol. The final expected free fatty acid goal was 0.05 mEq/g. The reaction reached completion 5.3 hours after heating began.

Example 2B

Tea/Fatty Acid Based Esteramine Synthesis with Phosphorous Acid Catalyst

Tallow fatty acid, 327.2 grams (MW=272.0, 1.203 mole) was placed into a small 4-neck round bottom flask, under a blanket of nitrogen. Triethanolamine (TEA), 94.5 grams (MW=149.19, 0.633 mole) was added to the flask, and the mole ratio of fatty acid/TEA was calculated to be 1.90/1. The mixture was stirred. The temperature of the mixture was increased to 130° C., at which point, phosphorous acid (MW=82.00, 0.2329 g, 0.002840 mole) was added to the reactor, which was then sealed under nitrogen. The nitrogen was subsurface sparged at a rate of 200 ml/min. The mixture was heated until a temperature of 170° C. was reached. The water was condensed with the help of an air cooled condenser. Samples of crude esteramine were collected at intervals and titrated for residual fatty acid with a visual phenolphthalein endpoint using 0.1000N KOH/Methanol. The final expected free fatty acid goal was 0.05 mEq/g. The reaction reached completion 6.1 hours after heating began.

Example 3

Tea/Fatty Acid Based Esteramine Synthesis with Zinc Derived from Zinc Stearate Tallow fatty acid (410.2 grams, MW=272.0, 1.508 mole) was placed into a small 4-neck round bottom flask at 85° C., under a blanket of nitrogen. Triethanolamine (TEA), 118.42 grams (MW=149.19, 0.7937 mole) was added to the flask, and the mole ratio of fatty acid/TEA was calculated to be 1.90/1. The mixture was stirred and heated to 130° C., at which point, zinc stearate (Sigma-Aldrich, technical grade, 0.5334 grams, 0.0008435 mole, MW=632.33) was added and the reactor was sealed under nitrogen. This amount gave a pre-reaction Zinc concentration of 104 ppm. The nitrogen was regulated and subsurface sparged at a rate of 200 mL/min. The mixture was heated until a temperature of 170° C. was reached. The water was condensed with the help of an air cooled condenser. Samples of crude esteramine were collected at intervals and titrated for residual fatty acid with a visual phenolphthalein endpoint using 0.1000N KOH/Methanol. The final expected free fatty acid goal was 0.06 mEq/g. The reaction reached completion 4.5 hours after Tmax was reached.

Example 4A

MDEA/Fatty Acid Based Esteramine Synthesis with Zinc Derived from Zinc Stearate Tallow fatty acid (839.0 g, 3.05 mole) was placed into a round bottom flask at 100° C., under a blanket of nitrogen. Methyldiethanolamine (220.7 g, 1.91 mole) was added to the flask. The zinc stearate was added at a loading level of 1000 ppm. This amount gave a pre-reaction Zinc concentration of about 100 ppm. The mixture was stirred and heated until a temperature of 190° C. was reached. The nitrogen was regulated and subsurface sparged at a rate of between 150 mL/min and 200 mL/min. The water was condensed with the help of an air cooled condenser. A vacuum of 160 mmHg was applied when the batch acid value reached 0.35 mEq/g or less. Samples of crude esteramine were collected at intervals and titrated for residual fatty acid with a visual phenolphthalein endpoint using 0.1000N KOH/Methanol. The final expected free fatty acid goal was 0.07 mEq/g. The reaction reached completion 2.25 hours after Tmax was reached. With phosphorous acid as the catalyst the reaction reached completion 4.67 hours after Tmax was reached. This represents a 51.8% reduction in reaction time as compared to standard.

Example 4B

MDEA/Fatty Acid Based Esteramine Synthesis with Phosphorous Acid Catalyst

Tallow fatty acid (194.0 g, 0.71 mole) was placed into a round bottom flask at 75° C., under a blanket of nitrogen. Methyldiethanolamine (50.5 g, 0.42 mole) was added to the flask. The phosphorous acid was added at a loading level of 500 ppm. The mixture was stirred and heated until a temperature of 175° C. was reached. The nitrogen was regulated and subsurface sparged at a rate of between 150 mL/min and 200 mL/min. The pressure was one atmosphere. The water was condensed with the help of an air cooled condenser. A sample of crude esteramine was collected one hour after Tmax was reached, then titrated for residual fatty acid with a visual phenolphthalein endpoint using 0.1000N KOH/Methanol. The one hour acid value was 0.294 mEq/g and will be used as the baseline for this study: Percent performance was equal to 1.00 units and set as the standard for comparison.

Example 4C

MDEA/Fatty Acid Based Esteramine Synthesis with Zinc Derived from Zinc Acetate Tallow fatty acid (195.9 g, 0.71 mole) was placed into a round bottom flask at 75° C., under a blanket of nitrogen. Methyldiethanolamine (51.5 g, 0.43 mole) was added to the flask. The zinc acetate was added at a loading level of 270 ppm. The mixture was stirred and heated until a temperature of 175° C. was reached. The nitrogen was regulated and subsurface sparged at a rate of between 150 mL/min and 200 mL/min. The pressure was one atmosphere. The water was condensed with the help of an air cooled condenser. A sample of crude esteramine was collected one hour after Tmax was reached, then titrated for residual fatty acid with a visual phenolphthalein endpoint using 0.1000N KOH/Methanol. The one hour acid value was 0.405 mEq/g: Percent performance was equal to 0.62 units if compared to the rate of the phosphorous acid catalyst reaction.

Example 4D

MDEA/Fatty Acid Based Esteramine Synthesis with Zinc Derived from Zinc Oxide Tallow fatty acid (198.8 g, 0.72 mole) was placed into a round bottom flask at 75° C., under a blanket of nitrogen.

Methyldiethanolamine (52.2 g, 0.44 mole) was added to the flask. The zinc oxide was added at a loading level of 120 ppm. The mixture was stirred and heated until a temperature of 175° C. was reached. The nitrogen was regulated and subsurface sparged at a rate of between 150 mL/min and 200 mL/min. The pressure was one atmosphere. The water was condensed with the help of an air cooled condenser. A sample of crude esteramine was collected one hour after Tmax was reached, then titrated for residual fatty acid with a visual phenolphthalein endpoint using 0.1000N KOH/Methanol. The one hour acid value was 0.291 mEq/g: Percent performance was equal to 1.01 units if compared to the rate of the phosphorous acid catalyst reaction.

Example 4E

MDEA/Fatty Acid Based Esteramine Synthesis with Zinc Derived from Zinc Oxide

Tallow fatty acid (198.0 g, 0.72 mole) was placed into a round bottom flask at 75° C., under a blanket of nitrogen. Methyldiethanolamine (51.9 g, 0.44 mole) was added to the flask. The zinc oxide was added at a loading level of 960 ppm. The mixture was stirred and heated until a temperature of 175° C. was reached. The nitrogen was regulated and subsurface sparged at a rate of between 150 mL/min and 200 mL/min. The pressure was one atmosphere. The water was condensed with the help of an air cooled condenser. A sample of crude esteramine was collected one hour after Tmax was reached, then titrated for residual fatty acid with a visual phenolphthalein endpoint using 0.1000N KOH/Methanol. The one hour acid value was 0.274 mEq/g: Percent performance was equal to 1.07 units if compared to the rate of the phosphorous acid catalyst reaction.

Example 4F

MDEA/Fatty Acid Based Esteramine Synthesis with Zinc Derived from Zinc Oxide

Tallow fatty acid (799.5 g, 2.91 mole) was placed into a round bottom flask at 75° C., under a blanket of nitrogen. Methyldiethanolamine (209.5 g, 1.76 mole) was added to the flask. The zinc oxide was added at a loading level of 2200 ppm. The mixture was stirred and heated until a temperature of 175° C. was reached. The nitrogen was regulated and subsurface sparged at a rate of between 150 mL/min and 200 mL/min. The pressure was one atmosphere. The water was condensed with the help of an air cooled condenser. A sample of crude esteramine was collected one hour after Tmax was reached, then titrated for residual fatty acid with a visual phenolphthalein endpoint using 0.1000N KOH/Methanol. The one hour acid value was 0.145 mEq/g: Percent performance was equal to 1.51 units if compared to the rate of the phosphorous acid catalyst reaction.

Example 5

DMEA/Methyl Ester Based Esteramine Synthesis with Sodium Methylate Catalyst

A mixture of dimethylethanolamine (DMEA 44.6 g, 0.50 mole) and 30% sodium methylate in methanol (1.1 g) was added to a 4-neck flask fitted with a nitrogen sparge, a distillation column, a thermocouple, and a mechanical stirrer. The mixture was heated to 130° C. after which a C12/C14 mixed fatty methyl ester (89.2 g 0.40 mole) was added. This mixture was heated to 155° C. and held there for 2 hrs. Conversion to the esteramine was determined by proton NMR to be 84%. Solids were observed.

Example 6

DMEA/Methyl Ester Based Esteramine Synthesis with Zinc Acetate Catalyst

A mixture of dimethylethanolamine (DMEA 68.3 g, 0.77 mole), C12/C14 mixed fatty methyl ester (90.5 g 0.41 mole), and zinc acetate (0.44 g) was added to a 4-neck flask fitted with a nitrogen sparge, a distillation column, a thermocouple, and a mechanical stirrer. The mixture was heated gradually to 180° C. over 4 hrs and held at 180° C. for 1.5 hrs. Conversion, as indicated by proton NMR, was 92%. The next day the mixture was reheated to 180° C. and held for 2 hours, the conversion, by proton NMR, was determined to be >99%. No solids were observed.

Example 7

DMEA/Methyl Ester Based Esteramine Synthesis with Titanium Catalyst

A mixture of dimethylethanolamine (DMEA, 114.5 g, 1.29 mole), C12/C14 mixed fatty methyl ester (270 g 1.21 mole), and Vertec 2000 a Titanium catalyst (0.27 g) was added to a 4-neck flask fitted with a nitrogen sparge, a distillation column, a thermocouple, and a mechanical stirrer. The mixture was heated from 140° C. to 152° C. over 5 hrs. Conversion to the esteramine was determined by proton NMR to be 24%.

Example 8

DMEA/Methyl Ester Based Esteramine Synthesis with Sodium Acetate Catalyst

A mixture of dimethylethanolamine (DMEA,116 g, 1.30 mole), C12/C14 mixed fatty methyl ester (236 g 1.06 mole), and sodium acetate catalyst (0.72 g) was added to a 4-neck flask fitted with a nitrogen sparge, a distillation column, a thermocouple, and a mechanical stirrer. The mixture was heated to 147° C. for 5 hrs. Conversion to the esteramine was determined by proton NMR to be 11%.

Example 9

Tea/Methyl Ester Based Esteramine Synthesis with Tetrabutyl Titinate Catalyst

A mixture of triethanolamine (TEA, 125 g, 0.84 mole), soft tallow methyl ester (379.2 g, 1.30 mole), tetrabutyl titinate (0.86 g), and Anox 20 anti-oxidant was added to a 4-neck flask fitted with a nitrogen sparge, a thermocouple, and a mechanical stirrer. The mixture was heated to 170° C. for 3 hrs. No methanol was observed in the overhead, which indicated a minimal conversion.

Selected example summaries are listed, as follows, in table form:

TABLE I

| Example Number | Temperature as Tmax | Catalyst Used | Reaction Time, Hours | Alkanolamine Used * |
|---|---|---|---|---|
| 1A | 180° C. | $Zn^{+2}$ | 0.75 | TEA |
| 1B | 180° C. | — | 1.37 | TEA |
| 2A | 170° C. | $Zn^{+2}$ | 5.3 | TEA |

TABLE I-continued

| Example Number | Temperature as Tmax | Catalyst Used | Reaction Time, Hours | Alkanolamine Used * |
|---|---|---|---|---|
| 2B | 170° C. | Phosphorous acid | 6.1 | TEA |
| 3 | 170° C. | $Zn^{+2}$ | 4.5 | TEA |

* Where TEA stands for Triethanolamine

TABLE II

| Example Number | Temperature as Tmax | Catalyst Used | Relative Reaction Performance※ | Alkanolamine Used ** |
|---|---|---|---|---|
| 4B | 175° C. | Phosphorous acid | 1.00 | MDEA |
| 4C | 175° C. | $Zn^{+2}$ | 0.62 | MDEA |
| 4D | 175° C. | $Zn^{+2}$ | 1.01 | MDEA |
| 4E | 175° C. | $Zn^{+2}$ | 1.07 | MDEA |
| 4F | 175° C. | $Zn^{+2}$ | 1.51 | MDEA |

※ Numbers larger than 1.00 are faster reaction rates.
** Where MDEA stands for Methyldiethanolamine.

The invention is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the invention as set forth in the appended claims.

What is claimed is:

1. A method for decreasing the reaction time between an alkanolamine and a fatty acid to produce esteramines, the method comprising:
   providing an alkanolamine;
   providing a fatty acid;
   reacting the alkanolamine and the fatty acid in the presence of a divalent zinc catalyst to form at least one esteramine, wherein the divalent zinc catalyst is present in an amount effective to decrease the reaction time compared to the reaction conducted with a Brønsted catalyst.

2. The method of claim 1, wherein the alkanolamine is selected from the group consisting of ethanolamine, diethanolamine, triethanolamine, triisopropanolamine, alkyldiethanolamines, alkyldiisopropanolamines, isopropanolamine, diisopropanolamine, dialkylmonoethanolamines, dialkylmonoisopropanolamines, and combinations thereof.

3. The method of claim 1, wherein the alkanolamine is triethanolamine.

4. The method of claim 1, wherein the divalent zinc catalyst comprises zinc oxide, zinc carbonate, or a zinc salt.

5. The method of claim 4, wherein the zinc salt is zinc diphosphinate, zinc triflate, or zinc stearate.

6. The method of claim 5, wherein the zinc diphosphinate catalyst is formed in situ.

7. The method of claim 1, wherein the reacting occurs at a temperature within the range of about 60° C. to about 300° C.

8. The method of claim 1, wherein the method occurs in the presence of an inert atmosphere.

9. The method of claim 8, wherein the inert atmosphere is nitrogen.

10. The method of claim 1, wherein the reacting occurs at a temperature within the range of about 130° C. to about 190° C.

11. The method of claim 1, wherein the fatty acid is an alkyl acid having from about 2 to about 30 carbon atoms.

12. The method of claim 11, wherein the alkyl acid has from about 5 to about 25 carbon atoms.

13. The method of claim 1, wherein the zinc catalyst is present in an amount greater than 1 ppm based on the total weight of the reactants.

14. The method of claim 1, wherein the zinc catalyst is present in an amount of about 20 ppm to about 5000 ppm based on the total weight of the reactants.

15. The method of claim 1, wherein the zinc catalyst is present in an amount of about 100 ppm to about 200 ppm based on the total weight of the reactants.

16. The method of claim 1, wherein the alkanolamine and fatty acid are present in a molar ratio of 0.5/1 to about 3/1, where the alkanolamine represents the denominator in the ratio.

17. A method for decreasing the reaction time of a reaction between an alkanolamine and a fatty acid by contacting with a divalent zinc catalyst selected from the group consisting of zinc oxide, zinc carbonate, zinc diphosphinate, zinc triflate, and zinc stearate,
   wherein the divalent zinc catalyst is present in an amount effective to decrease the reaction time compared to the reaction conducted with a Brønsted catalyst.

* * * * *